US007772283B2

(12) United States Patent
Treacy et al.

(10) Patent No.: US 7,772,283 B2
(45) Date of Patent: Aug. 10, 2010

(54) SYNERGISTIC INSECTICIDAL COMPOSITIONS

(75) Inventors: Michael Frank Treacy, Newtown, PA (US); Raymond Frank Borysewicz, Hamilton Square, NJ (US); Kurt Allen Schwinghammer, Yardley, PA (US); Paul E. Rensner, Yardley, PA (US); Hassan Oloumi-Sadeghi, Yardley, PA (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 11/931,102

(22) Filed: Oct. 31, 2007

(65) Prior Publication Data

US 2008/0139643 A1 Jun. 12, 2008

Related U.S. Application Data

(62) Division of application No. 10/145,784, filed on May 16, 2002, which is a division of application No. 09/521,987, filed on Mar. 9, 2000, now Pat. No. 6,479,543.

(60) Provisional application No. 60/124,306, filed on Mar. 12, 1999, provisional application No. 60/158,201, filed on Oct. 7, 1999.

(51) Int. Cl.
*A61K 31/175* (2006.01)
*C07C 337/06* (2006.01)
*C07C 337/08* (2006.01)
*C07C 281/06* (2006.01)
*C07C 281/08* (2006.01)
*C07C 281/14* (2006.01)

(52) U.S. Cl. .................. 514/581; 514/583; 514/590; 564/18; 564/20; 564/34; 564/36

(58) Field of Classification Search ..................... None
See application file for complete search history.

(56) References Cited

U.S. PATENT DOCUMENTS

| | | | |
|---|---|---|---|
| 4,663,341 A | 5/1987 | Jacobson | |
| 4,668,511 A | 5/1987 | Aspirot et al. | 424/93 |
| 4,731,385 A | 3/1988 | Tsuboi et al. | 514/789 |
| 4,742,060 A | 5/1988 | Shiokawa et al. | 514/252 |
| 5,093,362 A | 3/1992 | Milner et al. | |
| 5,116,850 A | 5/1992 | Stevenson | 514/341 |
| 5,232,940 A | 8/1993 | Hatton et al. | |
| 5,242,907 A | 9/1993 | Dawson | |
| 5,288,727 A | 2/1994 | Toki et al. | 514/632 |
| 5,304,573 A | 4/1994 | Hino et al. | 514/522 |
| 5,324,837 A | 6/1994 | Renga et al. | 544/333 |
| 5,369,121 A | 11/1994 | Harrison et al. | |
| 5,462,938 A | 10/1995 | Annus et al. | 514/229.8 |
| 5,543,573 A | 8/1996 | Takagi et al. | 514/590 |
| 5,662,897 A | 9/1997 | Miller et al. | 424/93.2 |
| 5,708,170 A | 1/1998 | Annis et al. | 544/212 |
| 5,843,981 A | 12/1998 | Miller | 514/421 |
| 5,858,353 A | 1/1999 | Miller et al. | 424/93.6 |
| 5,958,922 A | 9/1999 | McAuliffe et al. | |
| 5,972,971 A | 10/1999 | Heuer et al. | 514/341 |
| 6,057,355 A | 5/2000 | Haas et al. | |
| 6,156,309 A | 12/2000 | Miller et al. | 424/93.7 |
| 6,221,885 B1 | 4/2001 | Saito | |
| 6,338,846 B1 | 1/2002 | Kang et al. | 424/93.2 |
| 6,342,518 B1 | 1/2002 | Treacy et al. | 514/427 |
| 6,346,542 B1 | 2/2002 | Huber | |
| 6,479,543 B1 | 11/2002 | Treacy et al. | 514/522 |
| 6,506,556 B2 | 1/2003 | Treacy | 435/5 |
| 6,673,340 B1 | 1/2004 | Harrison et al. | 424/93.2 |
| 6,903,237 B2 | 6/2005 | Yamaguchi et al. | 564/20 |
| 2008/0106639 A1 | 5/2008 | Treacy et al. | 514/275 |
| 2008/0125420 A1 | 5/2008 | Treacy et al. | 514/229.2 |
| 2008/0125421 A1 | 5/2008 | Treacy et al. | 514/229.2 |
| 2008/0132470 A1 | 6/2008 | Treacy et al. | 514/86 |
| 2008/0132498 A1 | 6/2008 | Treacy et al. | 514/229.2 |
| 2008/0139542 A1 | 6/2008 | Treacy et al. | 514/229.2 |
| 2008/0139543 A1 | 6/2008 | Treacy et al. | 514/229.2 |
| 2008/0139658 A1 | 6/2008 | Treacy et al. | 514/590 |

FOREIGN PATENT DOCUMENTS

| | | |
|---|---|---|
| EP | 0 500 111 | 8/1992 |
| WO | WO 92/06076 | 4/1992 |
| WO | WO 96/03509 | 2/1996 |
| WO | WO 99/51721 | 10/1999 |

OTHER PUBLICATIONS

Yee et al., "Laboratory Evaluations of Synthetic and Natural Insecticides on Beet Armyworm (*Lepidoptera: Noctuidae*) Damage and Survival on Lettuce" Journal of Economic Entomology (1998) vol. 91 No. 1, pp. 56-63.*

Adan et al., "Laboratory Evaluation of the Novel Naturally Derived Compound Spinosad against *Ceratitis capitata*" Pesticide Science (1996) vol. 48 No. 3, pp. 261-268.*

Anonymous, Research Disclosure No. 39786, GB, Industrial Opportunities Ltd. Havant: "Mixtures of Arthropodicidfes and Fungicides;" May 1997, pp. 361-363.

(Continued)

*Primary Examiner*—Eric S Olson
(74) *Attorney, Agent, or Firm*—Novak Druce + Quigg LLP

(57) ABSTRACT

The present invention provides a synergistic insecticidal composition comprising as essential active ingredients a neuronal sodium channel antagonist in combination with one or more compounds selected from the group consisting of pyrethroids, pyrethroid-type compounds, recombinant nucleopolyhedroviruses capable of expressing an insect toxin, organophosphates, carbamates, formamidines, macrocyclic lactones, amidinohydrazones, GABA antagonists and acetylcholine receptor ligands.

Also provided are methods for synergistic insect control and crop protection.

10 Claims, No Drawings

OTHER PUBLICATIONS

Elbert et al., "*Imidacloprid, a novel systemic nitromethylene analogue insecticide for crop protection*"; Brighton Crop Protection Conference—Pests and Diseases 1990, 21-28.
Elbert et al., "*Imidacloprid—a new systemic insecticide*"; CAPLUS abstract No. 1995:187187, of Pflanzenschutz-Nachrichten Bayer (German Edition) 44(2), 113-136 (1991).
Worthing, The Pesticide Manual, $9^{th}$ Ed. 1991, The British Crop Protection Council [ISBN 0-948404-42-6] pp. 785, 831-834.
Nakagawa et al., "*Anti-insect toxin 5 (AaIT5) from Androctonus australis*" Eur. J. Biochem. 246, 496-501 (1997).
Jacques et al., "*Interaction of pyrethroids with the Na+ channel in mammalian neuronal cells in culture*" Biochim Biophys Acta 600(3), 882-97 (1980).
McCutchen et al., "*Interaction of Recombinant and Wild-Type Baculoviruses with Classical Insecticides and Pyrethroid-Resistant Tobacco Budworm*" J. Econ. Entomol. 90(5), 1170-80 (1997).
Maeda et al., "*Insecticidal effects of an insect-specific neurotoxin expressed by a recombinant baculovirus*" Virology 184(2), 777-80 (1991).
Payne et al., "*Structure-Activity Relationship for the Action of Dihydropyrazole Insecticides on Mouse Brain Sodium Channels*" Pestic. Biochem Physiol. 60, 177-185 (1998).
Wing et al., "*A Novel Oxadiazine Insecticide Is Bioactivated in Lepidopteran Larvae*" Arch. Insect Biochem. Physiol. 37, 91-103 (1998).
Treacy et al., "*Differential insecticidal properties exhibited against Heliothine spp. by two viral vectors encoding a similar chimeric toxin gene*" Proc. Beltwide Cotton Conf. 1999, 1076-1083.
Campanhola et al., "*Tobacco budworm resistance to pyrethroids: resistance spectra, synergists, and substitute insecticides*" Proc. Beltwide Cotton Conf. 1076-1083 (1988).
Bagwell et al., "Synergism of Insecticides Against Susceptible and Pyrethrod-Resistant Tobacco Budworms (*Lepidoptera: Noctuidae*) by Amitraz", J. Econ. Entomol. 85(3), 658-663 (1992).
Stark et al., "Toxicity, Penetration, and Metabolism of Acephate in Three Fruit Fly Species (*Diptera: Tephritidae*)" J. Econ. Entomol. 82(6), 1564-1571 (1989).
Liu et al., "Formamidines as Synergists of Cypermethrin in Susceptible and Pyrethroid Resistant House Flies (*Diptera: Muscidae*)" J. Econ. Entomol. 83(6), 2181-2186 (1990).
Eldoksch et al., "Toxicity and Synergism of Some Plant Extracts and Insecticides against European Corn Borer Egg-masses (*Lepidoptera: Pyralidae*)" Alex. Sci. Exch. 16(4), 495-502 (1995).
EXTONET PIP—Hydramethylnon, revised Jun. 1996 (Internet, http://extoxnet.orst.edu/pips/hydramet.htm).
Notice of Allowance issued Mar. 21, 2002 in parent U.S. Appl. No. 09/521,987, pp. 1-5.
Final Office action issued Dec. 21, 2001 in parent U.S. Appl. No. 09/521,987, cover page and pp. 1-4.
Non-final Office action issued Sep. 4, 2001 in parent U.S. Appl. No. 09/521,987, cover page and pp. 1-3.
Non-final Office action issued Mar. 28, 2001 in parent U.S. Appl. No. 09/521,987, cover page and pp. 1-7.
Restriction Requirement issued Oct. 4, 2000 in parent U.S. Appl. No. 09/521,987, pp. 1-5.
Final Office action issued May 21, 2009 in parent U.S. Appl. No. 10/145,784, cover page and pp. 1-12.
Non-final Office action issued Oct. 2, 2008 in parent U.S. Appl. No. 10/145,784, cover page and pp. 1-10.
Non-final Office action issued Jan. 3, 2008 in parent U.S. Appl. No. 10/145,784, cover page and pp. 1-11.
Non-final Office action issued May 4, 2006 in parent U.S. Appl. No. 10/145,784, cover page and pp. 1-14.
Non-final Office action issued Sep. 9, 2005 in parent U.S. Appl. No. 10/145,784, cover page and pp. 1-11.
Ex parte Quayle action issued Jun. 14, 2005 in parent U.S. Appl. No. 10/145,784, cover page and pp. 1-2.
Final Office action issued Nov. 13, 2003 in parent U.S. Appl. No. 10/145,784, cover page and pp. 1-4.
Non-final Office action issued Jan. 29, 2003 in parent U.S. Appl. No. 10/145,784, cover page and pp. 1-3.
Non-final Office action issued Sep. 11, 2002 in parent U.S. Appl. No. 10/145,784, cover page and pp. 1-3.
Non-final Office action issued May 7, 2009 in co-pending U.S. Appl. No. 11/930,344, cover page and pp. 1-7.
Restriction Requirement issued Dec. 11, 2008 in co-pending U.S. Appl. No. 11/930,344, cover page and pp. 1-5.
Final Office action issued May 14, 2009 in co-pending U.S. Appl. No. 11/930,612, cover page and pp. 1-11.
Non-final Office action issued Oct. 1, 2008 in co-pending U.S. Appl. No. 11/930,612, cover page and pp. 1-13.
Non-final Office action issued May 14, 2009 in co-pending U.S. Appl. No. 11/930,667, cover page and pp. 1-7.
Restriction Requirement issued Dec. 11, 2008 in co-pending U.S. Appl. No. 11/930,667, cover page and pp. 1-5.
Non-final Office action issued May 14, 2009 in co-pending U.S. Appl. No. 11/930,821, cover page and pp. 1-7.
Restriction Requirement issued Dec. 10, 2008 in co-pending U.S. Appl. No. 11/930,821, cover page and pp. 1-5.
Non-final Office action issued May 12, 2009 in co-pending U.S. Appl. No. 11/930,730, cover page and pp. 1-7.
Restriction Requirement issued Dec. 11, 2008 in co-pending U.S. Appl. No. 11/930,730, cover page and pp. 1-5.
Final Office action issued May 12, 2009 in co-pending U.S. Appl. No. 11/930,315, cover page and pp. 1-12.
Non-final Office action issued Oct. 1, 2008 in co-pending U.S. Appl. No. 11/931,315, cover page and pp. 1-13.
Non-final Office action issued Sep. 24, 2009 in co-pending U.S. Appl. No. 11/931,434, cover page and pp. 1-16.
Final Office action issued May 19, 2009 in co-pending U.S. Appl. No. 11/931,434, cover page and pp. 1-15.
Non-final Office action issued Oct. 2, 2008 in co-pending U.S. Appl. No. 11/931,434, cover page and pp. 1-15.
Restriction Requirement issued Dec. 10, 2008 in related U.S. Appl. No. 11/931,820, cover page and pp. 1-5.
Journal of Economic Entomology, vol. 90, No. 5, Oct. 1997, pp. 1170-1180.

* cited by examiner

SYNERGISTIC INSECTICIDAL COMPOSITIONS

CROSS-REFERENCE TO RELATED APPLICATIONS

This is a Divisional of application Ser. No. 10/145,784, filed on May 16, 2002, (pending), the entire disclosure of which is herewith incorporated by reference, which is a divisional application of application Ser. No. 09/521,987, filed on Mar. 9, 2000 (now U.S. Pat. No. 6,479,543), the entire disclosure of which is herewith incorporated by reference, which claims the benefit of provisional application Ser. No. 60/124,306 (filed Mar. 12, 1999) and Ser. No. 60/158,201 (filed on Oct. 7, 1999), the entire disclosures of which are herewith incorporated by reference.

BACKGROUND OF THE INVENTION

Insecticidal agents and compositions have been developed to control insect pests such as agrohorticultural pests, hygienic pests, or wood-eating pests and in practice have been used as a single or a mixed agent. However, economically efficient and ecologically safe insect control compositions are still being sought. Insecticidal compositions which allow for reduced effective dosage rates, increased environmental safety and lower incidence of insect resistance are highly desirable. Although the rotational application of insect control agents having different modes of action may be adopted for good pest management practice, this approach does not necessarily give satisfactory insect control. Further, even though combinations of insect control agents have been studied, a high synergistic action has not always been found. Obtaining an insecticidal composition which demonstrates no cross-resistance to existing insecticidal agents, no toxicity problems and little negative impact on the environment is extremely difficult.

Therefore, it is an object of this invention to provide a synergistic insecticidal composition which demonstrates a high controlling effect with concomitant reduced crop production cost and reduced environmental load.

It is another object of this invention to provide methods for synergistic insect control and enhanced crop protection.

SUMMARY OF THE INVENTION

The present invention provides a synergistic insecticidal composition comprising as essential active ingredients a synergistically effective amount of a neuronal sodium channel antagonist in combination with one or more compounds selected from the group consisting of pyrethroids, pyrethroid-type compounds, recombinant nucleopolyhedroviruses capable of expressing an insect toxin, organophosphates, carbamates, formamidines, macrocyclic lactones, amidinohydrazones, GABA (gamma-aminobutyric acid) antagonists, and acetylcholine receptor ligands.

The present invention also provides a method for synergistic insect control which comprises contacting said insect with a synergistically effective amount of a neuronal sodium channel antagonist in combination with one or more compounds selected from the group consisting of pyrethroids, pyrethroid-type compounds, recombinant nucleopolyhedroviruses capable of expressing an insect toxin, organophosphates, carbamates, formamidines, macrocyclic lactones, amidinohydrazones, GABA antagonists and acetylcholine receptor ligands.

The present invention further provides a method for the enhanced protection of plants from infestation and attack by insects.

DETAILED DESCRIPTION OF THE INVENTION

Definitions

"Acetylcholine receptor ligand compound" as used in this application means a compound which is capable of binding to the acetylcholine receptor site.

"Group A" as used in this application means insecticidal
1) pyrethroid compounds;
2) pyrethroid-type compounds;
3) recombinant nucleopolyhedroviruses capable of expressing an insect toxin;
4) organophosphate compounds;
5) carbamate compounds;
6) formamidine compounds;
7) macrocyclic lactone compounds;
8) amidinohydrazone compounds;
9) GABA antagonist compounds; and
10) acetylcholine receptor ligand compounds.

"Haloalkyl" as used in this application means an alkyl group $C_xH_{2x+1}$ having 1 to 2x+1 halogen atoms which may be the same or different, Similarly, the terms "haloalkenyl", "haloalkynyl", "haloalkoxy", "halophenyl" and the like mean mono- to perhalogen substitution wherein the halogens may be the same or different.

"Halogen" as used in this application means Cl, Br, I or F.

"Neuronal sodium channel antagonist" as used in this application means a compound which is capable of preventing the ability of a neuron cell to transfer sodium ions across the cell membrane.

"Pyrethroid-type compounds" as used in this application means those compounds characterized by a non-ester linked aryl-phenoxybenzyl moiety.

"Synergism" as used in this application means a cooperative action encountered in a combination of two or more biologically active components in which the combined activity of the two or more components exceeds the sum of the activity of each component alone.

Surprisingly, it has now been found that a composition which comprises a combination of a neuronal sodium channel antagonist and a second insecticidal ingredient provides superior insect control at lower levels of the combined active agents than may be achieved when the neuronal sodium channel antagonist or the second insecticidal ingredient is applied alone.

As previously stated, the term neuronal sodium channel antagonist designates a compound which is capable of preventing the ability of a neuron cell to transfer sodium ions across the cell membrane. A neuron cell thus affected is unable to fire, resulting in paralysis, and ultimately mortality, in the target host. Descriptions of neuronal sodium channel antagonists and their mode of action may be found in Pesticide Biochemistry and Physiology, 60: 177-185 or Archives of Insect Biochemistry and Physiology, 37: 91-103.

Neuronal sodium channel antagonists include compounds such as those described in U.S. Pat. No. 5,543,573; U.S. Pat. No. 5,708,170; U.S. Pat. No. 5,324,837 and U.S. Pat. No. 5,462,938, (the description of which are hereby incorporated by reference) among other publications. Exemplary of the neuronal sodium channel antagonist compounds useful in the composition of this invention are those compounds having the structural formula

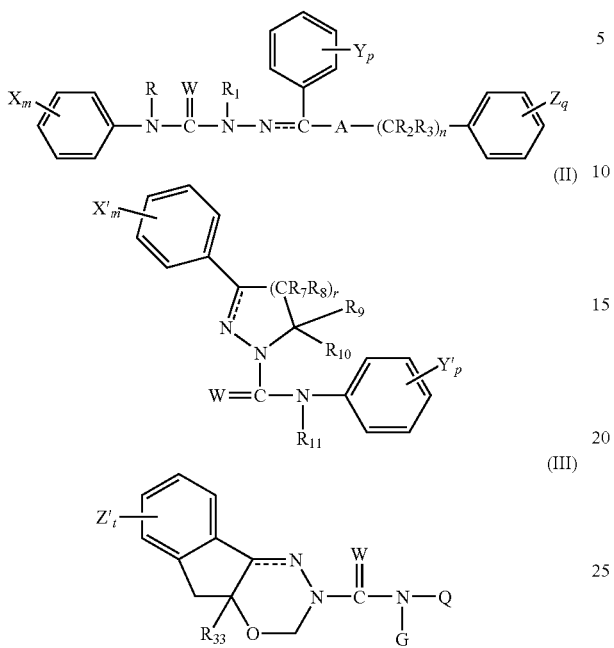

wherein A is $CR_4R_5$ or $NR_6$;
W is O or S;
X, Y, Z, X', Y' and Z' are each independently H; halogen; OH; CN; $NO_2$; $C_1$-$C_6$alkyl optionally substituted with one or more halogen, $C_1$-$C_3$alkoxy, $C_1$-$C_3$haloalkoxy, $C_3$-$C_6$cycloalkyl, $C_2$-$C_6$alkenyloxy or sulfonyloxy groups;
$C_1$-$C_6$alkoxy optionally substituted with one or more halogen, $C_1$-$C_3$alkoxy or $C_3$-$C_6$cycloalkyl groups;
$C_1$-$C_6$alkoxycarbonyl, $C_3$-$C_6$cycloalkylcarbonyloxy, phenyl optionally substituted with one or more halogen, $C_1$-$C_4$alkyl, or $C_1$-$C_4$alkoxy groups;
aminocarbonyloxy optionally substituted with one or more $C_1$-$C_3$alkyl groups;
$C_1$-$C_6$alkoxycarbonyloxy; $C_1$-$C_6$alkylsulfonyloxy; $C_2$-$C_6$alkenyl; or $NR_{12}R_{13}$;
m, p and q are each independently an integer of 1, 2, 3, 4, or 5;
n is an integer of 0, 1 or 2;
r is an integer of 1 or 2;
t is an integer of 1, 2, 3 or 4;
R, $R_1$, $R_2$, $R_3$, $R_4$ and $R_5$ are each independently H or $C_1$-$C_4$alkyl;
$R_6$ is H, $C_1$-$C_6$alkyl, $C_1$-$C_6$haloalkyl, $C_1$-$C_6$alkoxyalkyl, $C_1$-$C_6$alkoxy, $C_1$-$C_6$haloalkoxy, $C_2$-$C_6$alkenyl, $C_2$-$C_6$alkynyl, $C_1$-$C_6$alkylcarbonyl, $C_1$-$C_6$alkoxy-carbonyl, $C_1$-$C_6$alkylthio, or $C_1$-$C_6$haloalkylthio;
$R_7$ and $R_8$ are each independently H; halogen; $C_1$-$C_6$alkyl; $C_1$-$C_6$alkylcarbonyloxy; or phenyl optionally substituted with one or more halogen, CN, $NO_2$, $C_1$-$C_6$alkyl, $C_2$-$C_6$haloalkyl, $C_1$-$C_6$alkoxy or $C_1$-$C_6$haloalkoxy groups;
$R_9$ and $R_{10}$ are each independently H, or $C_1$-$C_4$alkyl;
$R_{11}$ is H, $C_1$-$C_6$alkyl, $C_1$-$C_6$haloalkyl, $C_1$-$C_4$alkylcarbonyl, $C_1$-$C_6$alkoxycarbonyl, or $C_1$-$C_6$haloalkoxycarbonyl;
$R_{12}$ and $R_{13}$ are each independently H or $C_1$-$C_6$alkyl;

G is H, $C_1$-$C_6$alkyl, optionally substituted with one or more halogen, $C_1$-$C_4$alkoxy, $C_1$-$C_6$haloalkoxy, CN, $NO_2$, $S(O)_uR_{14}$, $COR_{15}$, $CO_2R_{16}$, phenyl or $C_3$-$C_6$cycloalkyl groups;
$C_1$-$C_6$alkoxy; $C_1$-$C_6$haloalkoxy; CN; $NO_2$; $S(O)_uR_{17}$; $COR_{18}$; $CO_2R_{19}$; phenyl optionally substituted with one or more halogen, CN, $C_1$-$C_3$halo-alkyl, or $C_1$-$C_3$haloalkoxy groups;
$C_3$-$C_6$cycloalkyl; or phenylthio;
Q is phenyl optionally substituted with one or more halogen, CN, SCN, $NO_2$, $S(O)_uR_{20}$, $C_1$-$C_4$alkyl, $C_1$-$C_4$haloalkyl, $C_1$-$C_4$alkoxyalkyl, $C_1$-$C_6$haloalkoxy, or $NR_{21}R_{22}$ groups;
u is an integer of 0, 1 or 2;
$R_{14}$, $R_{15}$, $R_{16}$, $R_{18}$, $R_{19}$, $R_{21}$ and $R_{22}$ are each independently H or $C_1$-$C_6$alkyl;
$R_{17}$ and $R_{20}$ are each independently $C_1$-$C_6$alkyl or $C_1$-$C_6$haloalkyl;
$R_{33}$ is $CO_2R_{34}$;
$R_{34}$ is H, $C_1$-$C_6$alkyl, $C_1$-$C_6$haloalkyl, phenyl or halophenyl; and the dotted line configuration C---N represents a double bond or a single bond (i.e. C—N or C=N); or
a stereoisomer thereof.

Preferred neuronal sodium channel antagonists suitable for use in the composition of the invention are those compounds of formula I, II or III wherein the dotted line configuration C---N represents a double bond.

More preferred neuronal sodium channel antagonists suitable for use in the inventive composition are those compounds of formula I or formula III wherein the dotted line configuration represents a double bond.

Particularly preferred neuronal sodium channel antagonists useful in the composition of the invention are those compounds of formula I or formula III wherein W is O; X is trifluoromethoxy and is in the 4-position; Y is trifluoromethyl and is in the 3-position; Z is CN and is in the 4-position; A is $CH_2$; n is 0; m, p and q are each 1; R and $R_1$ are each H; $Z_1$ is $C_1$; $R_{33}$ and G are each $CO_2CH_3$; Q is p-(trifluoromethoxy) phenyl; and the dotted line configuration C---N represents a double bond; or a stereoisomer thereof.

Further neuronal sodium channel antagonist compounds include those described in U.S. Pat. No. 5,116,850 and U.S. Pat. No. 5,304,573, (the description of which are hereby incorporated by reference) among other publications. Exemplary of further neuronal sodium channel antagonist compounds suitable for use in the composition of the invention are those compounds having structural formula

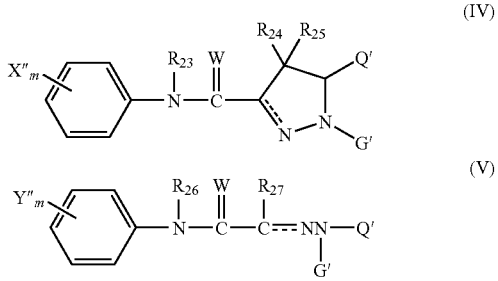

wherein W is O or S;
X" and Y" are each independently H; halogen; CN; SCN; $C_1$-$C_6$alkyl optionally substituted with one or more halogen, $NO_2$, CN, $C_1$-$C_4$alkoxy, $C_1$-$C_4$alkylthio, phenyl, halophenyl, $C_1$-$C_4$alkylsulfonyl, $C_1$-$C_4$haloalkylsulfonyl, or $C_1$-$C_4$alkoxycarbonyl groups;

$C_2$-$C_4$alkenyl; $C_2$-$C_4$haloalkenyl; $C_2$-$C_4$alkynyl; $C_2$-$C_4$haloalkynyl; $C_3$-$C_6$cycloalkyl; $C_3$-$C_6$halocycloalkyl; phenyl optionally substituted with one or more halogen, CN, $NO_2$, $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$alkylsulfonyl or $C_1$-$C_4$haloalkylsulfonyl groups;

$C_1$-$C_4$alkylcarbonyl; $C_1$-$C_4$haloalkylcarbonyl; or $NR_{28}R_{29}$;

m is an integer of 1, 2, 3, 4 or 5;

G' is phenyl optionally substituted with one or more groups which may be the same or different selected from X";

a 5-membered heteroaromatic ring containing one or two heteroatoms selected from 0 or 1 oxygen, 0 or 1 sulfur and 0, 1 or 2 nitrogen atoms said 5-membered heteroaromatic ring being attached via carbon and being optionally substituted with one or more groups which may be the same or different selected from X"; or a 6-membered heteroaromatic ring containing one or two heteroatoms selected from 0 or 1 oxygen, 0 or 1 sulfur and 0, 1 or 2 nitrogen atoms said 6-membered heteroaromatic ring being attached via carbon and being optionally substituted with one or more groups which may be the same or different selected from X";

Q' is H; $C_1$-$C_6$alkyl optionally substituted with one or more halogen, CN, $C_1$-$C_3$alkoxy, $C_1$-$C_6$alkoxycarbonyl, or phenyl optionally substituted with one or more halogen, CN, $NO_2$, $C_1$-$C_4$alkyl, $C_1$-$C_4$haloalkyl, $C_1$-$C_4$alkylsulfonyl or $C_1$-$C_4$alkylsulfinyl groups;

$C_2$-$C_6$alkenyl; $C_2$-$C_6$alkynyl; or phenyl optionally substituted with one to three groups, which may be the same or different, selected from X";

$R_{23}$, $R_{24}$, $R_{25}$, $R_{26}$, $R_{27}$, $R_{28}$ and $R_{29}$ are each independently H or $C_1$-$C_4$alkyl; and the dotted line configuration C$\cdots$N represents a double bond or a single bond (i.e. C—N or C=N); or a stereoisomer thereof.

Further preferred neuronal sodium channel antagonist compounds of the invention are those compounds of formula IV or V wherein the dotted line configuration C$\cdots$ represents a double bond.

Other preferred neuronal sodium channel antagonist compounds suitable for use in the composition of the invention are those compounds of formula IV or V wherein W is O; X" and Y" are each independently H or $C_1$-$C_6$haloalkyl; m is 1; $R_{23}$, $R_{24}$, $R_{25}$, $R_{26}$ and $R_{27}$ are each H; G' is phenyl optionally substituted with one or more halogen atoms; Q' is halophenyl or $C_1$-$C_4$alkyl optionally substituted with one phenyl or halophenyl group; and the dotted line configuration C$\cdots$N represents a double bond; or a stereoisomer thereof.

The second active ingredient of the insecticidal composition of the invention includes one or more compounds selected from Group A:

1) pyrethroid compounds which are known to be insecticidally active such as cypermethrin, cyhalothrin, cyfluthrin, permethrin or the like;

2) pyrethroid-type compounds which are known to be insecticidally active such as ethofenprox, silafluofen, or the like;

3) recombinant nucleopolyhedroviruses capable of expressing an insect toxin, preferably an insect neurotoxin such as Androctonus australis insect toxin (AaIT), for example HzNPV-AaIT;

4) organophosphate compounds which are known to be insecticidally active such as profenofos, acephate, sulprofos, malathion, diazinon, methyl parathion, terbufos, or the like;

5) carbamate compounds which are known to be insecticidally active such as methomyl, thiodicarb, fenothiocarb, or the like;

6) formamidine compounds which are known to be insecticidally active such as amitraz, chlordimeform, chlorfenamidine, or the like;

7) macrocyclic lactone compounds which are known to be insecticidally active such as spinosad, avermectin, emamectin, milbemectin, nemadectin, moxidectin or the like;

8) amidinohydrazone compounds which are known to be insecticidally active such as hydramethylnon;

9) GABA antagonist compounds which are known to be insecticidally effective such as fipronil, endosulfan, or the like;

10) acetylcholine receptor ligand compounds which are known to be insecticidally effective such as imidacloprid, acetamiprid, nitenpyram, thiamethoxam, or the like.

Descriptions of the above-listed commercially available compounds may be found in The Pesticide Manual, 11th Edition, British Crop Protection Council (1997) among other publications. Descriptions of recombinant nucleopolyhedroviruses capable of expressing an insect toxin include Treacy et al, Proceedings Beltwide Cotton Conference (1999), pp 1076-1083.

Preferred compositions of the invention are those compositions having a neuronal sodium channel antagonist compound of formula I or formula III in combination with one or more compounds selected from Group A.

More preferred compositions of the invention are those compositions having a formula I or formula III compound wherein W is O; X is trifluoromethoxy and is in the 4-position; Y is trifluoromethyl and is in the 3-position; Z is CM and is in the 4-posiotion; A is $CH_2$; n is 0; m, p and q are each independently 1; R and $R_1$ are each independently H; Z' is Cl; $R_{33}$ and G are each independently $CO_2CH_3$; Q is p-(trifluoromethoxy)phenyl; and the dotted line configuration C$\cdots$N represents a double bond in combination with one or more compounds selected from Group A.

Each of the compounds of formula I, II, III, IV and V embody asymmetric centers which may be represented in the stereoisomeric R-form or S-form. The present invention also includes the R-form, the S-form or mixtures comprising the R-form and the S-form in an arbitrary ratio. For compounds of formula III, the S-form is preferred.

Advantageously, the neuronal sodium-channel antagonist compound of formula I, II, III, IV or V or a mixture thereof may be formulated with a second insecticidally effective ingredient and optionally other customary formulation adjuvants. Said formulation may be dispersed in a solid or liquid diluent for application to the insect, its food supply, breeding ground or habitat as a dilute spray or as a solid dust or dust concentrate.

The active ingredients of the inventive composition may also be formulated separately as a wettable powder, emulsifiable concentrate, aqueous or liquid flowable, suspension concentrate or any one of the conventional formulations used for insect control agents and tank-mixed in the field with water or other inexpensive liquid for application as a liquid spray mixture. The separately formulated compositions may also be applied sequentially.

Advantageously, the composition of the invention may be formulated as a bait composition comprising a synergistically effective amount of a combination of a neuronal sodium channel antagonist plus one or more compounds selected from Group A and a solid or liquid edible nutritive substance. A preferred bait composition may contain by weight about 0.01% to 20% active ingredients, preferably a neuronal sodium channel antagonist in combination with hydramethylnon.

In actual practice, the composition of the invention may be applied to the plant foliage or plant stem or to the insect habitat or to the locus of a hygienic pest as a dilute spray prepared from any of the above-said formulations. The ratio of the essential active ingredients of the composition of the invention is about 1 weight part of a neuronal sodium channel antagonist to about 0.01-100 weight parts of one or more compounds selected from Group A.

The compositions of the invention are superior insecticidal compositions and are especially useful for the control of agrohorticultural pests, hygienic pests or wood-eating pests. Said compositions are highly effective for the protection of growing and harvested plants including: leguminous crops such as soybeans, snap beans, peas, wax beans and the like as well as cotton, forage crops, cole crops, leafy vegetables, tobacco, hops, tomatoes, potatoes, flowering ornamentals such as chrysanthemums, vine crops such as grapes, squash, pumpkin or melon and fruit trees such as cherry, peach, apple or citrus, from the ravages of insects.

The synergistic insecticidal composition of the invention is found to be highly active against a wide variety of lepidopteran and coleopteran insects such as *Helicoverpa zea* (cotton bollworm), *Heliothis virescens* (tobacco budworm), *Leptinotarsa decemlineata* (Colorado potato beetle), *Diabrotica* spp. (corn rootworm) and the like.

Beneficially, the composition of the invention may be useful for the prevention and control of hygienic or public health pests such as: Diptera, e.g. houseflies, mosquitoes, or the like; Hymenoptera, e.g. ants, parasitic wasps, wasps or the like; Blattaria, e.g. cockroaches; or the like.

Further, the compositions of the invention may be particularly useful for the prevention and control of wood-eating insects such as termites (Isoptera), carpenter ants (Hymenoptera), wood-destroying beetles (Coleoptera) or the like.

These and other advantages of the invention may become more apparent from the examples set forth herein below. These examples are provided merely as illustrations of the invention and are not intended to be construed as a limitation thereof.

Example 1

Evaluation of the Synergistic Insecticidal Effect of a Combination of a Neuronal Sodium Channel Antagonist Plus a Second Insecticide In this evaluation, *Heliothis zea* (cotton bollworm), *Heliothis virescens* (tobacco budworm) and pyrethroid-resistant *Heliothis virescens* larvae used are obtained from laboratory colonies. Pyrethroid-resistant *H. virescens* are derived from the PEG-strain [Campannola & Plapp, Proceedings of Beltwide Cotton Conference (1988)].

Cotton leaves are immersed in 1:1 v/v, acetone/water solutions of test compound, or solutions of a combination of test compounds for a period of about 3 seconds. Following immersion, leaves are allowed to air-dry for 2-3 hours. Plastic bioassay trays containing multiple open-faced wells (4.0× 4.0×2.5 cm) are used as the test arenas. Cut portions of a treated leaf, a moistened cotton dental wick and a single third-instar larva are placed into each well, covered with an adhesive vented clear plastic sheet and held under constant fluorescent light at about 27° C. for a predetermined period of time. Larval mortality/morbidity is evaluated at 5 days after treatment. All treatments are replicated 4-5 fold in a randomized complete block design with 16-32 larvae per treatment. Using conventional log-probit analysis, the $LC_{50}$ of each treatment is determined.

Using the above protocol, a neuronal sodium channel antagonist (Compound A) may be evaluated alone at dose rates of 0.1 ppm, 1.0 ppm and 10.0 ppm and in combination with 1.0 ppm of a second insecticidal compound. Treatments which may be used are shown in Table I.

TABLE I

| Second Active Compound | Dose Rate (ppm) | Compound A1 Dose Rate | | |
|---|---|---|---|---|
| | | (ppm) | (ppm) | (ppm) |
| cypermethrin | 0 | 0.1 | 1.0 | 10.0 |
| | 1.0 | 0.1 | 1.0 | 10.0 |
| amitraz | 0 | 0.1 | 1.0 | 10.0 |
| | 1.0 | 0.1 | 1.0 | 10.0 |
| fipronil | 0 | 0.1 | 1.0 | 10.0 |
| | 1.0 | 0.1 | 1.0 | 10.0 |
| acetamiprid | 0 | 0.1 | 1.0 | 10.0 |
| | 1.0 | 0.1 | 1.0 | 10.0 |
| spinosad | 0 | 0.1 | 1.0 | 10.0 |
| | 1.0 | 0.1 | 1.0 | 10.0 |
| thiodicarb | 0 | 0.1 | 1.0 | 10.0 |
| | 1.0 | 0.1 | 1.0 | 10.0 |

[1]Compound A = formula Ia neuronal sodium channel antagonist

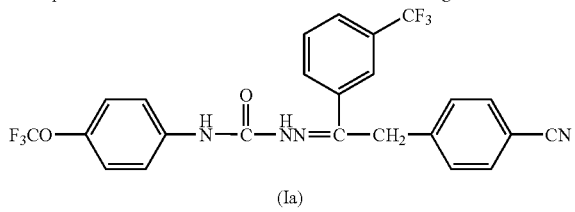

(Ia)

Example 2

Evaluation of the Synergistic Insecticidal Effect of a Combination of a Neuronal Sodium Channel Antagonist Plus an Amidinohydrazone In this evaluation, adult male German cockroaches (*Blattella germanica*) are used. For each test, a 4.0 g portion of ground Purina Dog Chow (Hi-Pro Glo®) is treated with an acetone solution of test compound alone or in combination with a second test compound. After treatment, the acetone is evaporated and the treated dog chow is placed in a ¾ oz plastic cup which is placed in a harborage made of folded sheets of blotter paper placed in a plastic box (16" L×11" W×6" H). The plastic box (test arena) is also fitted with a 1 oz narrow mouth bottle with 2 dental wicks inserted at the mouth. A control box is prepared in the same manner using ground dog chow which has been treated with reagent grade acetone. Each treatment is replicated three times. Into each test arena are placed 20 healthy adult male cockroaches which have been reared in an insectary. The test arenas are then stored at 76° F. and mortality is determined daily by visual examination. The data obtained are shown in Table 11.

TABLE II

| Test Compound | % Active Ingredient | % Mortality Days After Treatment | | | | | |
|---|---|---|---|---|---|---|---|
| | | 3 | 4 | 5 | 6 | 7 | 8 |
| A[1] | 0.05 | 0 | 0 | 0 | 0 | 0 | 0 |
| A | 0.10 | 1.7 | 11.7 | 11.7 | 11.7 | 18.3 | 18.3 |
| A | 0.50 | 5.0 | 5.0 | 5.0 | 5.0 | 5.0 | 5.0 |
| B[2] | 1.00 | 0 | 5.0 | 28.3 | 71.7 | 90.0 | 93.3 |
| A + B | 0.05 + 1.0 | 0 | 20.0 | 41.7 | 81.7 | 95.0 | 98.3 |
| A + B | 0.10 + 1.0 | 0 | 21.7 | 51.7 | 88.3 | 95.0 | 95.0 |
| A + B | 0.50 + 1.0 | 16.7 | 58.3 | 80.0 | 95.0 | 98.3 | 100.0 |
| Control | 0 | 0 | 0 | 1.7 | 3.3 | 3.3 | 5.0 |

[1]Compound A = formula Ia neuronal sodium channel antagonist
[2]Compound B = hydramethylnon (structure of compound Ia)

(Ia)

As can be seen from the data shown in Table II, combinations of a neuronal sodium channel antagonist plus an amidinohydrazone insecticide demonstrate synergistic insect control.

Example 3

Evaluation of the Synergistic Insecticidal Effect of a Combination of a Neuronal Sodium Channel Antagonist Plus a Recombinant Nucleopolyhedrovirus Capable of Expressing an Insect Toxin In this evaluation, *Helicoverpa zea* (cotton bollworm) larvae are obtained from a laboratory colony. Test compounds are dissolved in 1:1 v/v acetone/water. Plastic bioassay trays (C-D International, Pitman, N.J.) are used as test arenas. Each tray contains 32 open-faced wells, 4.0×4.0×2.5 cm. A portion (5 ml) of a wheat germ-soybean flour-based artificial diet (Southland Products, Lake village, AR) is poured into each well. After the diet hardened, 0.4 ml of test solution is pipetted onto the diet surface in each well. Test solutions are evenly spread over surfaces of diet by picking up the tray and gently tilting it from side to side. Trays are then held in a vented area for about 2 h, until water is no longer pooled on diet surfaces. A single 4-day-old *H. zea* larva is then placed on the surface of diet in each well. After larval infestation, each well is covered with an adhesive, vented, clear plastic sheet.

All test arenas are held under constant fluorescent light and a temperature of about 27° C. for duration of the assay. Larval mortality is determined at 2, 3, 4 and 7 days after treatment. A larva was considered to be dead if it exhibited little to no movement, even after being shaken in the diet tray. A total of 32 insects were tested for each treatment. The data obtained are shown in Table III.

TABLE III

| Test Compound | Conc. of Active Ingredient | % Mortality Days After Treatment | | | |
|---|---|---|---|---|---|
| | | 2 | 3 | 4 | 7 |
| A[1] | 0.1 ppm | 43.8 | 46.9 | 53.1 | 53.1 |
| B[2] | 1000 OB[3]/ml | 3.1 | 34.4 | 50.5 | 62.5 |
| B | 500 OB/ml | 0.0 | 9.4 | 18.8 | 40.6 |
| B | 100 OB/ml | 3.1 | 3.1 | 3.1 | 15.6 |
| A + B | 0.1 + 1000 | 87.5 | 90.6 | 93.8 | 96.9 |
| A + B | 0.1 + 500 | 75.0 | 78.1 | 84.4 | 87.5 |
| A + B | 0.1 + 100 | 62.5 | 75.0 | 75.0 | 78.1 |
| Control | 0 | 3.1 | 3.1 | 3.1 | 3.1 |

[1]Compound A = formula Ia neuronal sodium channel antagonist
[2]Compound B = HzNPV-AaIT, *Helicoverpa zea* Nucleopolyhedrovirus which expresses *Androctonus australis* insect toxin
[3]OB = viral occlusion bodies (structure of compound Ia)

(Ia)

As can be seen from the data shown in Table III, combinations of a neuronal sodium channel antagonist plus a recombinant nucleopolyhedrovirus which is capable of expressing an insect toxin demonstrate synergistic insect control.

What is claimed is:

1. A synergistic insecticidal composition comprising a synergistically effective amount of a neuronal sodium channel antagonist in combination with one or more macrocyclic lactone compounds selected from the group consisting of spinosad, avermectin, emamectin, milbemectin, nemadectin, and moxidectin, wherein the neuronal sodium channel antagonist is a compound of formula (I)

(I)

(structure of formula I)

wherein
  A is $CR_4R_5$ or $NR_6$;
  W is O or S;
  X, Y and Z, are each independently H; halogen; OH; CN; $NO_2$; $C_1$-$C_6$ alkyl optionally substituted with one or more halogen, $C_1$-$C_3$ alkoxy, $C_1$-$C_3$ haloalkoxy, $C_3$-$C_6$ cycloalkyl, $C_2$-$C_6$ alkenyloxy or sulfonyloxy groups; $C_1$-$C_6$ alkoxy optionally substituted with one or more halogen, $C_1$-$C_3$ alkoxy or
  $C_3$-$C_6$ cycloalkyl groups;
  $C_1$-$C_6$ alkoxycarbonyl, $C_3$-$C_6$ cycloalkylcarbonyloxy, phenyl optionally substituted with one or more halogen, $C_1$-$C_4$ alkyl, or $C_1$-$C_4$ alkoxy groups;
  aminocarbonyloxy optionally substituted with one or more $C_1$-$C_3$ alkyl groups;
  $C_1$-$C_6$ alkoxycarbonyloxy; $C_1$-$C_6$ alkylsulfonyloxy; $C_2$-$C_6$ alkenyl; or $MR_{12}R_{13}$;

m, p and q are each independently an integer of 1, 2, 3, 4, or 5;

n is an integer of 0, 1 or 2;

R, $R_1$, $R_2$, $R_3$, $R_4$ and $R_5$ are each independently H or $C_1$-$C_4$alkyl;

$R_6$ is H, $C_1$-$C_6$ alkyl, $C_1$-$C_6$ haloalkyl, $C_1$-$C_6$ alkoxyalkyl, $C_1$-$C_6$ alkoxy, $C_1$-$C_6$ haloalkoxy, $C_2$-$C_6$ alkenyl, $C_2$-$C_6$ alkynyl, $C_1$-$C_6$ alkylcarbonyl, $C_1$-$C_6$ alkoxycarbonyl, $C_1$-$C_6$ alkylthio, or $C_1$-$C_6$ haloalkylthio;

$R_{12}$ and $R_{13}$ are each independently H or $C_1$-$C_6$ alkyl;

and the dotted line configuration C---N represents a double bond or a single bond; or a stereoisomer thereof.

2. The composition according to claim 1 wherein the dotted line configuration C---N represents a double bond.

3. The composition according to claim 2 wherein W is O; X is trifluoromethoxy and is in the 4-position; Y is trifluoromethyl and is in the 3-position; Z is CN and is in the 4-position; A is $CH_2$; n is 0; m, p and q are each 1; R and $R_1$ are each independently H.

4. A method for synergistic insect control which comprises contacting said insects with a synergistically effective amount of a neuronal sodium channel antagonist in combination with one or more insecticidally active macrocyclic lactone compounds selected from the group consisting of spinosad, avermectin, emamectin, milbemectin, nemadectin, and moxidectin, wherein the neuronal sodium channel antagonist is a compound of formula (I)

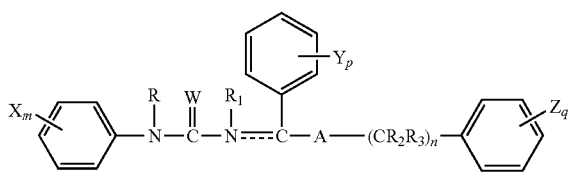

wherein

A is $CR_4R_5$ or $NR_6$;

W is O or S;

X, Y and Z, are each independently H; halogen; OH; ON; $NO_2$; $C_1$-$C_6$ alkyl optionally substituted with one or more halogen, $C_1$-$C_3$ alkoxy, $C_1$-$C_3$ haloalkoxy, $C_3$-$C_6$ cycloalkyl, $C_2$-$C_6$ alkenyloxy or sulfonyloxy groups; $C_1$-$C_6$ alkoxy optionally substituted with one or more halogen, $C_1$-$C_3$ alkoxy or $C_3$-$C_6$ cycloalkyl groups;

$C_1$-$C_6$ alkoxycarbonyl, $C_3$-$C_6$ cycloalkylcarbonyloxy, phenyl optionally substituted with one or more halogen, $C_1$-$C_4$ alkyl, or $C_1$-$C_4$ alkoxy groups;

aminocarbonyloxy optionally substituted with one or more $C_1$-$C_3$ alkyl groups;

$C_1$-$C_6$ alkoxycarbonyloxy; $C_1$-$C_6$ alkylsulfonyloxy; $C_2$-$C_6$ alkenyl; or $MR_{12}R_{13}$;

m, p and q are each independently an integer of 1, 2, 3, 4, or 5;

n is an integer of 0, 1 or 2;

R, $R_1$, $R_2$, $R_3$, $R_4$ and $R_5$ are each independently H or $C_1$-$C_4$alkyl;

$R_6$ is H, $C_1$-$C_6$ alkyl, $C_1$-$C_6$ haloalkyl, $C_1$-$C_6$ alkoxyalkyl, $C_1$-$C_6$ alkoxy, $C_1$-$C_6$ haloalkoxy, $C_2$-$C_6$ alkenyl, $C_2$-$C_6$ alkynyl, $C_1$-$C_6$ alkylcarbonyl, $C_1$-$C_6$ alkoxycarbonyl, $C_1$-$C_6$ alkylthio, or $C_1$-$C_6$ haloalkylthio;

$R_{12}$ and $R_{13}$ are each independently H or $C_1$-$C_6$ alkyl;

and the dotted line configuration C---N represents a double bond or a single bond; or a stereoisomer thereof.

5. The method according to claim 4, wherein the dotted line configuration C---N represents a double bond.

6. The method according to claim 5, wherein W is O; X is trifluoromethoxy and is in the 4-position; Y is trifluoromethyl and is in the 3-position; Z is CN and is in the 4-position; A is $CH_2$; n is 0; m, p and q are each 1; R and $R_1$ are each independently H.

7. The method according to claim 4, wherein the insect is selected from the group consisting of Blattaria, Isoptera, Diptera, and Hymenoptera.

8. The method according to claim 4, wherein the insects are lepidoptera or coleoptera.

9. A method for protecting a plant from infestation and attack by insects which comprises applying to the foliage or stem of said plant a synergistically effective amount of a composition according to claim 1.

10. The method according to claim 9, wherein the dotted line configuration C---N represents a double bond; W is O; X is trifluoromethoxy and is in the 4-position; Y is trifluoromethyl and is in the 3-position; Z is CN and is in the 4-position; A is $CH_2$; n is 0; m, p and q are each 1; R and $R_1$ are each independently H.

* * * * *

UNITED STATES PATENT AND TRADEMARK OFFICE
CERTIFICATE OF CORRECTION

| | | |
|---|---|---|
| PATENT NO. | : 7,772,283 B2 | |
| APPLICATION NO. | : 11/931102 | |
| DATED | : August 10, 2010 | |
| INVENTOR(S) | : Treacy et al. | |

It is certified that error appears in the above-identified patent and that said Letters Patent is hereby corrected as shown below:

In Claim 1, col. 1, indicated lines 40-50:

" 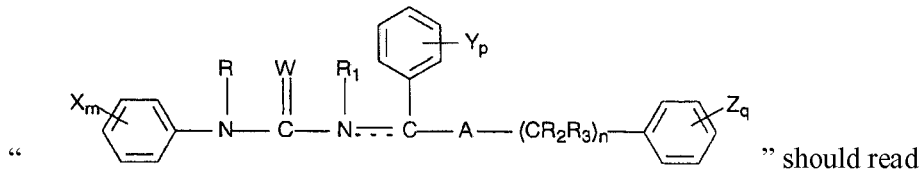 " should read

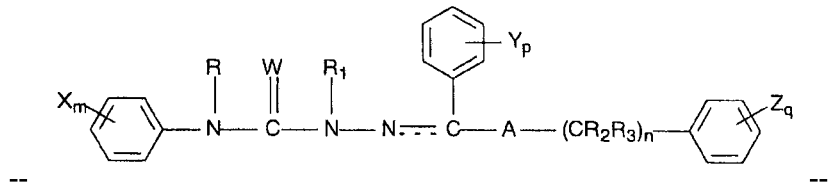

--                                                                                --

In Claim 1, col. 11, indicated line 1:
"$MR_{12}R_{13}$" should read -- $NR_{12}R_{13}$ --

In Claim 4, col. 1, indicated lines 31-40:

" 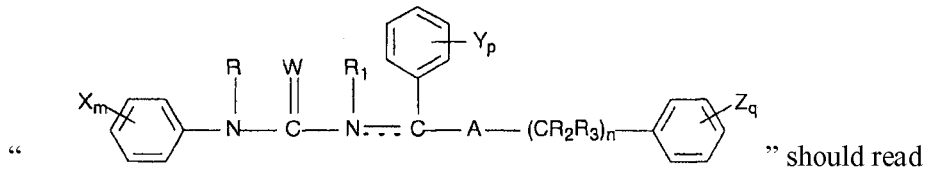 " should read

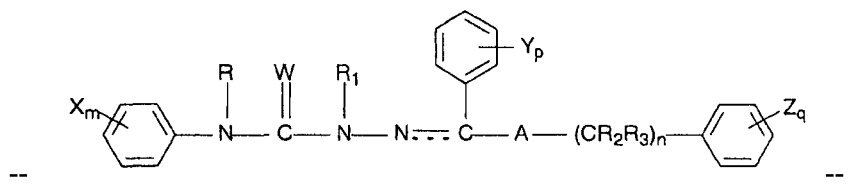

--                                                                                --

Signed and Sealed this
Twelfth Day of April, 2011

David J. Kappos
*Director of the United States Patent and Trademark Office*

CERTIFICATE OF CORRECTION (continued)
U.S. Pat. No. 7,772,283 B2

In Claim 4, col. 11, indicated line 45:
"ON" should read -- CN --

In Claim 4, col. 12, indicated line 12:
"$MR_{12}R_{13}$" should read -- $NR_{12}R_{13}$ --